(12) United States Patent  
Mews et al.

(10) Patent No.: US 8,603,155 B2  
(45) Date of Patent: Dec. 10, 2013

(54) STENT HAVING IMPROVED STENT DESIGN

(75) Inventors: Steffen Mews, Rostock (DE); Frank Bakczewitz, Rostock (DE)

(73) Assignee: BIOTRONIK VI Patent AG, Baar (CH)

( * ) Notice: Subject to any disclaimer, the term of this patent is extended or adjusted under 35 U.S.C. 154(b) by 0 days.

(21) Appl. No.: 13/344,142

(22) Filed: Jan. 5, 2012

(65) Prior Publication Data

US 2012/0101566 A1    Apr. 26, 2012

Related U.S. Application Data

(63) Continuation of application No. 12/777,644, filed on May 11, 2010, now abandoned.

(60) Provisional application No. 61/218,999, filed on Jun. 22, 2009.

(51) Int. Cl.
*A61F 2/06* (2013.01)

(52) U.S. Cl.
USPC .......................................................... 623/1.16

(58) Field of Classification Search
USPC .............................................. 623/1.11–1.54
See application file for complete search history.

(56) References Cited

U.S. PATENT DOCUMENTS 6,066,169 A * 5/2000 McGuinness ................. 623/1.16  
6,773,455 B2   8/2004 Allen et al.

2001/0016770 A1 * 8/2001 Allen et al. ................... 623/1.15  
2002/0123799 A1   9/2002 Burgermeister  
2003/0004566 A1   1/2003 Dang et al.  
2004/0230293 A1  11/2004 Yip et al.  
2006/0173530 A1   8/2006 Das

FOREIGN PATENT DOCUMENTS

EP         1 095 631 A2    5/2001  
WO   WO 2006/099449 A3    9/2006

* cited by examiner

*Primary Examiner* — David Isabella  
*Assistant Examiner* — Ann Schillinger  
(74) *Attorney, Agent, or Firm* — Biotech Beach Law Group PC

(57) ABSTRACT

A stent is provided having a base body circumscribing a cylindrical shape and radially expandable from a contracted starting position into a dilated support position, including a plurality of meander-shaped struts disposed in the circumferential direction and arrayed on one another in the axial direction, each strut being meander-shaped in its coarse structure and made of a flexible material, and at least one axial connector in the axial direction, connecting the meander-shaped struts of two axially adjacent meandering curves, wherein the at least one axial connector connects the inside radius of a zenith point of a first meandering curve with a second meandering curve, characterized in that the at least one axial connector at the inside radius of the zenith point of the first meandering curve has an at least double-arm structure.

10 Claims, 8 Drawing Sheets

STENT HAVING IMPROVED STENT DESIGN

CROSS REFERENCE TO RELATED APPLICATIONS

This invention is a continuation of U.S. patent application Ser. No. 12/777,644, filed May 11, 2010, which itself claims benefit of priority to U.S. provisional patent application Ser. No. 61/218,999, filed on Jun. 22, 2009, now expired; the contents of each are herein incorporated by reference in their entirety.

FIELD OF THE INVENTION

The invention relates to a stent having improved stent design.

BACKGROUND OF THE INVENTION

Implantation of stents has become established as one of the most effective therapeutic measures for treatment of vascular diseases. Stents assume a supporting function in the hollow organs of a patient. Stents of conventional construction have a base body with a plurality of circumferential support structures. For example, metallic struts have a base body which is initially in a compressed form for insertion into the body and then is dilated at the site of use. One of the main areas for use of such stents is for permanently or temporarily widening and keeping open of vascular obstructions, in particular constrictions (stenoses) of the coronary vessels. In addition, aneurysm stents are known that serve to support damaged vascular walls or seal off intracerebral vascular bulges.

Conventional stents for the treatment of stenoses have a cylindrical base body of sufficient load-bearing capacity that opens the constricted vessel and keeps it open to the desired degree to restore unobstructed blood flow. The circumferential wall of the base body is typically formed by a lattice-like bearing structure, allowing for the stent to be inserted in a compressed (crimped) state with a small outside diameter up to the point of constriction of the vessel to be treated, and to be sufficiently widened, e.g., by means of a dilatation balloon catheter until the vessel has the desired increased inside diameter. The steps of placing and expanding the stents during this procedure and their final positioning in the tissue upon completion of the procedure must be monitored by the cardiologist. This may be accomplished by means of imaging methods such as x-ray examinations.

The stent has a basic body made of an implant material. An implant material is a nonviable material that is used in medicine and interacts with biological systems. The basic prerequisite for the use of a material as implant material that is in contact with the physical body environment during its intended use is its physical compatibility (biocompatibility). Biocompatibility refers to the ability of a material to induce an appropriate tissue reaction in a specific application. This includes adaptation of the chemical, physical, biological and morphological surface properties of an implant to the recipient tissue with the goal of clinically desirable interaction. The biocompatibility of the implant material further depends on the chronological course of reaction of the biosystem in which it is implanted. Irritations and inflammations may occur at relatively short notice and cause tissue changes. Biological systems thus react in different ways, depending on the properties of the implant material. According to the reaction of the biosystem, implant materials may be categorized as bioactive, bioinert and biodegradable/resorbable materials.

Stents have a cylindrical base body including a lumen along the axial direction. The base body has a plurality of meander-shaped struts, forming the circumferential support structures, e.g. circumferential cylindrical meandering rings or helices, arranged one after the other along the axial direction. The support structures are connected in the axial direction by means of connecting elements, so-called axial connectors or connectors. At least in vascular support stents these axial connectors must on the one hand be arranged in such a manner that sufficient bending flexibility of the stent is guaranteed, and on the other hand they should not obstruct the crimping and/or dilatation processes.

U.S. Pat. No. 6,464,720 proposes a stent design in which the stent base body has apertures. These apertures serve to accommodate radiopaque markers made of a material that does not allow the passage of x-rays. While the apertures in this stent design only minimally affect crimpability, they hinder homogenous plastic deformation of the support elements and thus have a significant negative impact on the mechanical properties of the stent.

A cause for increased vascular inflammatory reactions upon stent implantation is the targeted use of stent overdilatation, which is necessitated by a certain spring-back of the stent shortly after implantation, so-called recoil. Such recoil, whose degree depends on the respective design and, particularly, the material used, is shown by any material composition used for implants. To achieve a minimum lumen size that is physiologically reasonable for the treated vessel after implantation, overdilatation of the stent is necessary to offset recoil. This overdilatation causes the vessel to be overstretched so that vessel damage occurs, causing the body to respond with an inflammatory reaction and subsequent increased formation of new tissue (neointimal proliferation). Both reactions need to be minimized in the context of stent implantations.

Especially when using magnesium or a magnesium alloy as a degradable stent material, it is particularly important, due to their not very favorable mechanical material properties, to minimize the effects on the distribution of forces, combined with an effective utilization of crimp space, which calls for optimal design of the axial connectors.

SUMMARY OF THE INVENTION

The present invention is targeted at solving the above mentioned problems. In particular, a stent design is to be provided that allows for minimum impact on the distribution of forces in the supporting struts while effectively utilizing the space available for crimping and at the same time allowing for homogeneous plastic deformation, particularly during dilatation of the stent base body at the treatment site. In particular, recoil of the stent body following implantation is to be kept at a minimum.

This problem is solved by providing a stent having a base body circumscribing a cylindrical shape and being radially expandable from a contracted starting position into a dilated support position, including a plurality of meander-shaped struts disposed in the circumferential direction and arrayed on one another in the axial direction, each strut being meander-shaped in its coarse structure and made of a flexible material, and at least one axial connector in the axial direction, connecting the meander-shaped struts of two axially adjacent meandering curves, wherein the at least one axial connector connects the inside radius of a zenith point of a first meandering curve with a second meandering curve, wherein the at least one axial connector, at the inside radius of the zenith point of the first meandering curve, has an at least double-arm structure.

The solution according to the invention is characterized in that the at least one axial connector connecting the meander-shaped struts joins with the inside radius of the zenith point in an at least double-arm structure. Due to this at least double-arm structure of the connection between the meander-shaped strut and the axial connector, homogeneous distribution of strains and stresses in the curved elements of the stent remains unaffected. Homogeneous plastic deformability of the stent of the invention is thus ensured. Due to the at least double-arm structure, additional plastic deformation areas are created in the stent system as a whole, which adds to reinforcing the system.

Due to joining the at least double-arm structure of the axial connector to the inside radius of the zenith point, the joint only takes up little space so that enough space is available to ensure sufficient crimpability and bending flexibility of the stent of the invention.

Due to the joining sites of the at least double-arm structure of the axial connector being distributed over the entire inside radius of the zenith point, the stent according to the invention provides an optimal distribution of forces from one support structure to the next, as well as the required stability. Alignment of the axial connectors substantially along the axial direction of the stent results in optimal utilization of space in the crimped state of the stent of the invention.

Due to the at least double-arm structure of the axial connectors of the stent according to the invention, the axial connectors support the stent in its standard and radial forces. The radial force is the force that is perpendicular to the axial direction and radially pointing outward, imparting to the stent the support properties to keep the lumen of the blood vessel open. Due to the connection by means of the at least double-arm structure, apertures are formed between the arms of the at least double-arm structure and the inner radius of the joined zenith point. These apertures constitute closed cells in the stent structure, increasing stent stiffness and thus contributing to reinforcing the whole system. Due to the stiffening of the entire system, recoil of the system as a whole is minimized. Therefore, by means of the at least double-arm structure, the axial connectors contribute to increasing the radial force, and thus the supporting force of the stent, and keep undesired recoil at a minimum.

In a preferred embodiment, the at least double-arm structure includes two arms. In the dilated support position of the stent upon implantation, the two arms of the at least double-arm structure enclose an angle in the range of 30° to 180°, preferably in the range of 60° to 180°, and particularly preferred in the range of 90° to 180°.

In another preferred embodiment, the at least double-arm structure includes three arms. The middle one of the three arms runs parallel to the axial direction of the stent. The overall arrangement of the arms is in symmetry relative to the axial direction. Asymmetrical arrangements, however, are also possible and feasible.

The base body of the stent according to the invention may be made of any implantation material suitable for the production of implants, particularly stents. Implant materials for stents include polymers, metallic materials and ceramic materials. Biocompatible metals and metal alloys for permanent implants include, for example, stainless steels (such as 316L), cobalt base alloys (such as CoCrMo casting alloys, CoCrMo forge alloys, CoCrWNi forge alloys, and CoCrNiMo forge alloys), pure titanium and titanium alloys (such as cp titanium, $TiAl_6V_4$ or $TiAl_6Nb_7$), and gold alloys. Preferably, the base body includes a metallic implant material.

Particularly preferred, the stent according to the invention has a base body including a biodegradable implant material. In the field of biodegradable stents, magnesium or pure iron as well as biodegradable base alloys of the elements magnesium, iron, zinc, molybdenum, and tungsten are used. In particular, the base body of a stent according to the invention may include a biodegradable magnesium alloy.

For the purposes of the present invention, "alloy" is meant to designate a metallic lattice whose main component is magnesium, iron, zinc or tungsten. The main component is the alloy component having the highest percentage by weight of the alloy. Preferably, a main component percentage is more than 50% by weight, in particular more than 70% by weight.

It is not imperative that both the base body and the at least one axial connector be made of the same material. In fact, any combination of materials—metals and polymers—is possible. When using biodegradable stents care is to be taken that all the materials used are biodegradable.

BRIEF DESCRIPTION OF THE DRAWINGS

The invention is described based on the attached drawings.

DETAILED DESCRIPTION OF THE INVENTION

Figure 1A:
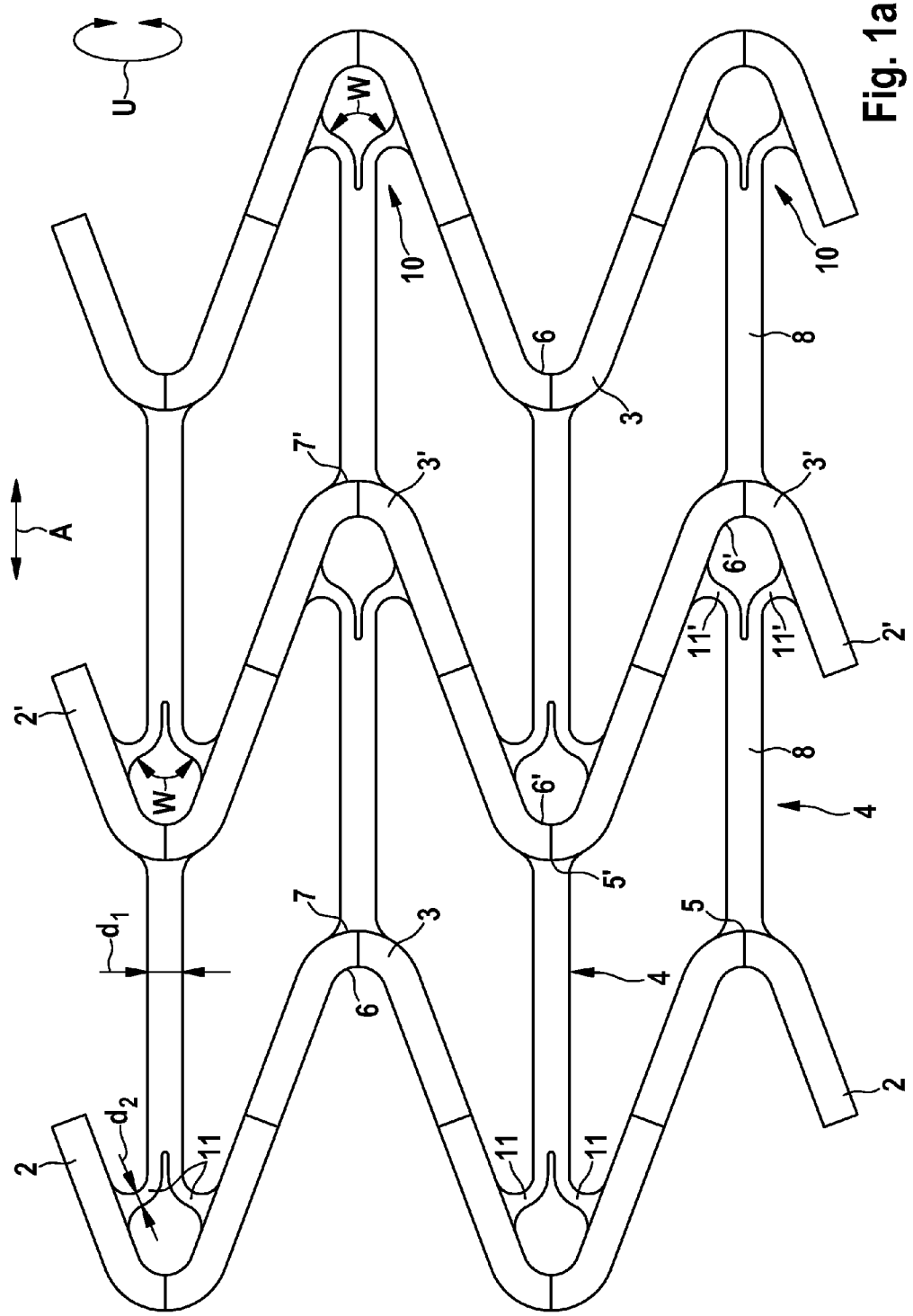
FIG. 1a schematically shows a section of a base body of the stent according to the invention, wherein the at least double-arm structure consists of exactly two arms, and the axial connector in each case connects the inside radius of the zenith point of the first meandering curve with the outside radius of the zenith point of the second meandering curve.

The invention will subsequently be explained in greater detail on the basis of the exemplary embodiments in conjunction with the figures.

A stent has a base body circumscribing a cylindrical shape and enclosing a lumen along an axial direction. Upon implantation of the stent into a blood vessel, the blood flow can be effected through this lumen. The base body includes a plurality of meander-shaped struts disposed in the circumferential direction and arrayed on one another in the axial direction, each strut being meander-shaped in its coarse structure and made of a flexible material. The meander-shaped struts are substantially responsible for the support function of the stent. The necessary expansion of the stent base body upon stent implantation is ensured by the meandering shape of the struts.

The meandering shape has zenith points alternating their direction of curving in the course of the meander-shaped strut. A right curve is followed by a left curve, with a short straight segment of the meander-shaped strut in between. This system continues along the axial direction in an alternating manner such that a ring-shaped circumferential structure is formed, enclosing a lumen. The zenith points have an inside radius and an outside radius. The inside radius of the zenith point is the zone lying inside the circle, if the zenith point is conceived as part of a circular shape. Correspondingly, the outside radius is the outside boundary of the imagined circular shape of the zenith point.

Besides having a plurality of support structures, the base body includes one or more axial connectors, thus enabling two successive circumferential support structures to be connected with each other by at least one axial connector. The axial connectors of the stent according to the invention are designed to allow for connecting a plurality of support structures to form one base body that is suitable for use in an expandable stent. For this purpose, one axial connector in each case connects a zenith point of a first meandering curve of a meander-shaped strut with a second meandering curve of an axially adjacent meander-shaped strut. The zenith points of the first and second meandering curves lie in the axial-parallel direction, or in opposite directions to each other, or in an offset pattern, respectively, so that the axial connector runs along the length of the cylindrical area of the base body. Two successive meander-shaped struts may also be connected with each other by more than one axial connector. Preferably, the axial connectors are just long enough to provide sufficient flexibility of the two neighboring meander-shaped struts, but not so long that the stent of the invention will become torsion-soft. One or more or all of the axial connectors of a stent according to the invention may have a curved shape. The axial connectors are aligned in a substantially axial direction between the two circumferential meander-shaped struts to be connected, but the axial connectors are not necessarily arranged in exactly parallel alignment to the axial direction.

The stent according to the invention includes axial connectors having an elongated shape. The axial connector is composed of a main stem and the at least double-arm structure. The main stem of the axial connector passes directly and immediately into the at least double-arm structure. The at least double-arm structure connects the axial connector with the inside radius of the zenith point of the meander-shaped strut. The at least double-arm structure of the axial connector consists of at least two arms. The at least two arms of the axial connector constitute the joining of the main stem with the inside radius of the zenith point of the meander-shaped strut.

The main stem of the axial connector has a web width $d_1$, and the arms of the at least double-arm structure have a web width $d_2$, with $d_1$ being greater than $d_2$. The diameters of the arms, however, may also have different sizes.

At both of its ends the axial connector has joints with the meander-shaped strut. At the joints of the at least double-arm structure the at least two arms pass into the inside radius of the zenith point of the meander-shaped structure. The joining site of the arms, however, may also be located in the straight segment of the meandering curve.

Joining the at least one axial connector with the second meandering curve is accomplished either by means of joining with an outside radius of the zenith point of the second meandering curve, an inside radius of the zenith point of the second meandering curve, or a point on the straight connection between the inside radius and the outside radius of the second meandering curve ("strut"). The joining of the at least one axial connector with the second meandering curve may also be effected by a multiple-arm structure.

The web width of the at least two arms of the double-arm structure and the web width of the main stem at the joint immediately before the transition to the meander-shaped structure are larger than the respective web widths $d_1$ and $d_2$, respectively. The web width of the joints tapers continuously towards the axial connectors. This tapering may be homogeneous, but it may also be uneven.

FIG. 1a shows a section of a base body of a stent according to the invention. What is shown are sections of two meander-shaped struts 2 and 2' disposed in the circumferential direction U and arrayed on one another in the axial direction A, which are connected with each other by means of axial connectors 4. The meander-shaped struts 2 and 2' have meandering curves 3 and 3'. The meandering curves 3 and 3' show zenith points 5 and 5', having an inside radius 6, 6' and an outside radius 7, 7'. The axial connectors 4 connect the inside radius 6 of the zenith point 5 with the outside radius 7' of the zenith point 5' of the meander-shaped strut 2' adjacent in the axial direction A. The at least double-arm structure is accomplished in FIG. 1a by two arms 11 and 11', respectively.

The axial connector 4 is composed of a main stem 8 and the double-arm structure 10. The main stem 8 of the axial connector passes directly and immediately into the double-arm structure 10. The main stem 8 of the axial connector has a web width $d_1$, and the two arms 11 and 11', respectively, of the double-arm structure 10 have a web width $d_2$, with $d_1$ being greater than $d_2$.

In the embodiment having a double-arm structure, the two arms together with the inside radius of the zenith point of the meandering curve define an aperture having a ladle-like shape.

Figure 1B:
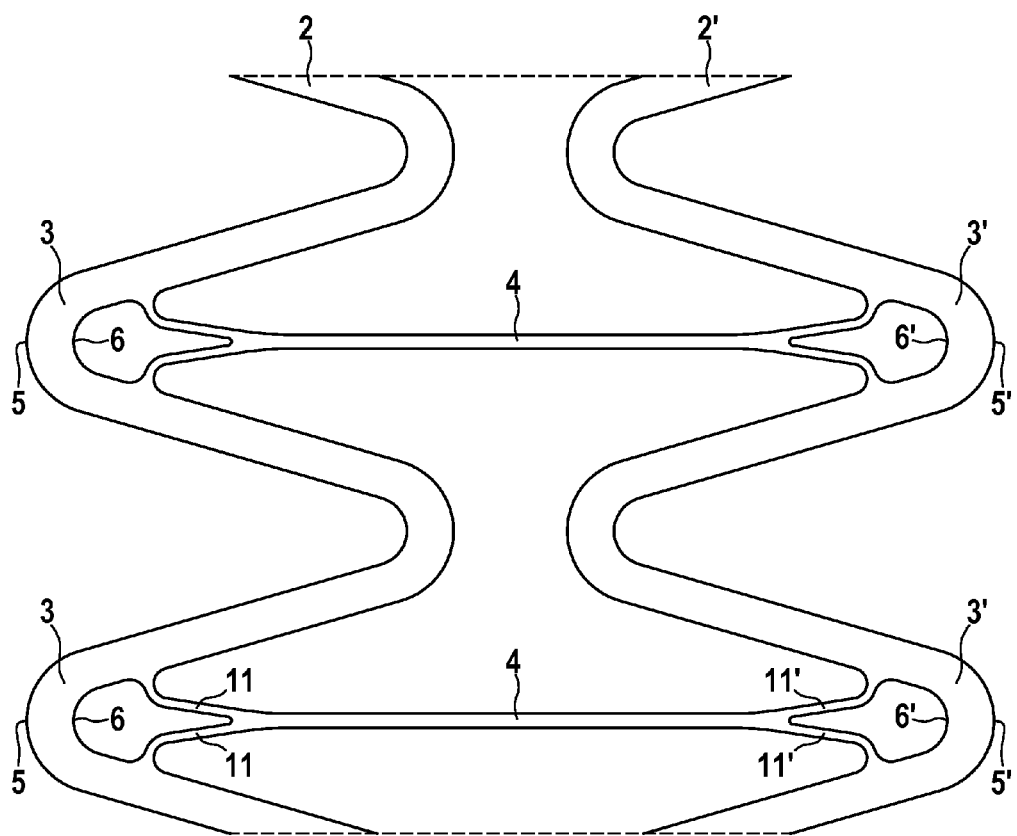
FIGS. 1b and 1c schematically show sections of a base body of a stent according to the invention, wherein the at least double-arm structure consists of exactly two arms, and the axial connector in each case connects the inside radius of a zenith point of a first meandering curve with the inside radius of the zenith point of a second meandering curve.
Figure 1C:
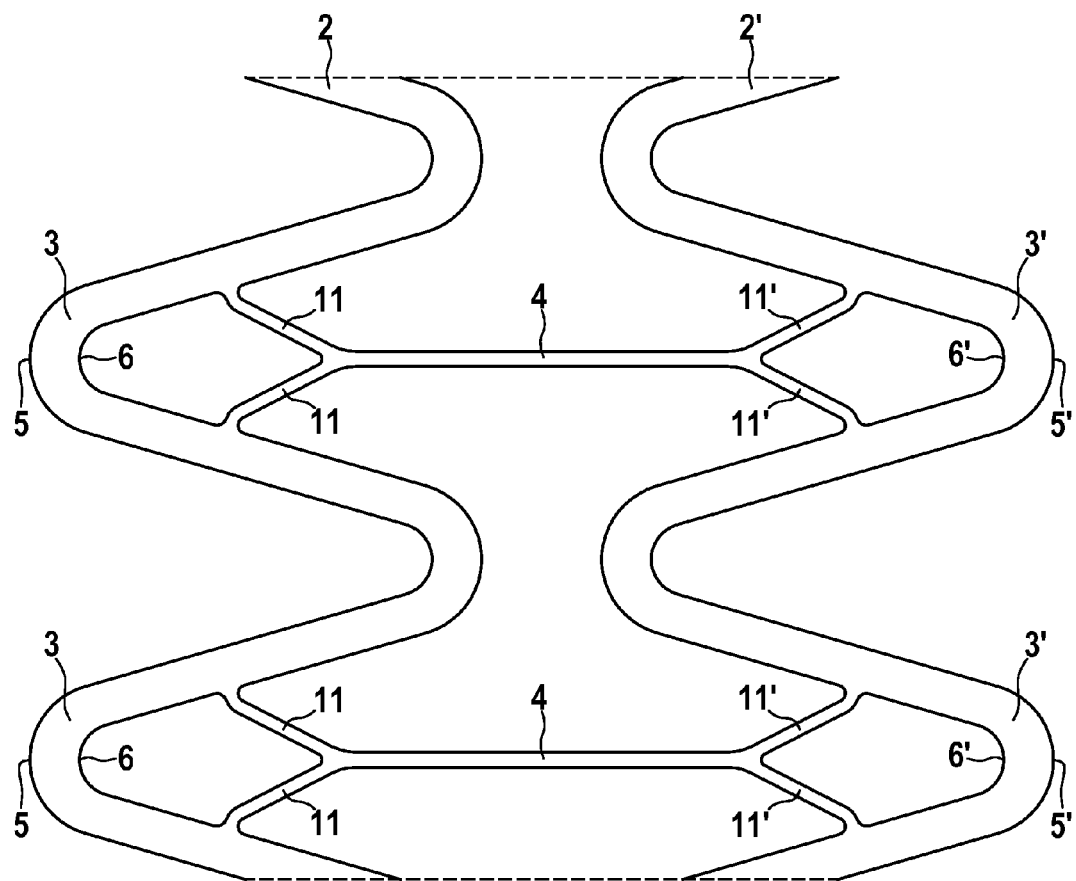

FIGS. 1b and 1c show sections of a base body of a stent according to the invention. What is shown are sections of two meander-shaped struts 2 and 2' disposed in the circumferential direction U and arrayed on one another in the axial direction A, which are connected with each other through axial connectors 4. The meander-shaped struts 2 and 2' have meandering curves 3 and 3'. The meandering curves 3 and 3' show zenith points 5 and 5', having an inside radius 6 and an outside radius 7. What is shown are two different variants of a so-called valley-to-valley connection; this means that the axial connectors 4 connect the inside radius 6 of the zenith point 5 with the inside radius 6' of the zenith point 5' of the meander-shaped strut 2' adjacent in the axial direction A. The at least double-arm structure is accomplished in FIGS. 1b and 1c by two arms 11 and two arms 11'.

Figure 1D:
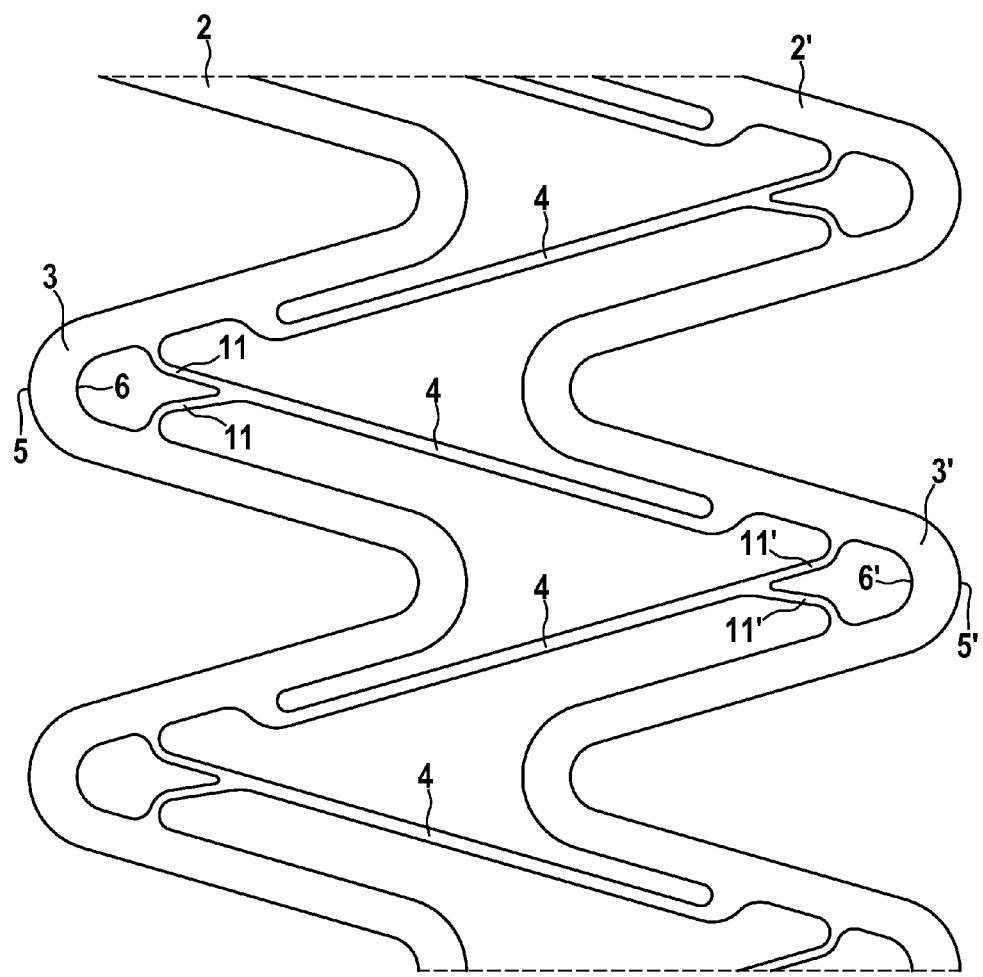
FIGS. 1d and 1e schematically show sections of a base body of a stent according to the invention, wherein the at least double-arm structure consists of exactly two arms, and the axial connector in each case connects the inside radius of a zenith point of a first meandering curve with the straight segment of a second meandering curve.
Figure 1E:
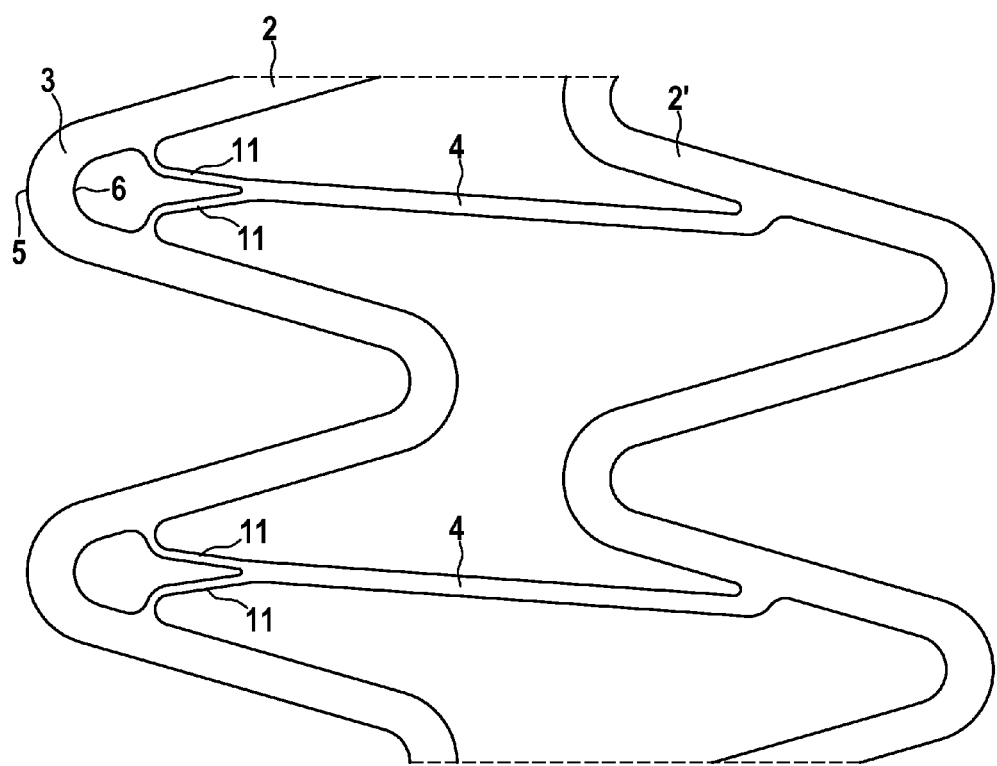

FIGS. 1d and 1e show sections of a base body of a stent according to the invention. What is shown are sections of two meander-shaped struts 2 and 2' disposed in the circumferential direction U and arrayed on one another in the axial direction A, which are connected with each other through axial connectors 4. The meander-shaped struts 2 and 2' have meandering curves 3 and 3'. The meandering curves 3 and 3' show zenith points 5 and 5', having an inside radius 6 and an outside radius 7. What is shown are two different variants of a so-called valley-to-strut connection; this means that the axial connectors 4 connect the inside radius 6 of the zenith point 5 with the straight segment of the meander-shaped strut 2' adjacent in the axial direction A. The at least double-arm structure in FIGS. 1d and 1e is accomplished by means of two arms 11 and two arms 11'.

Figure 2A:
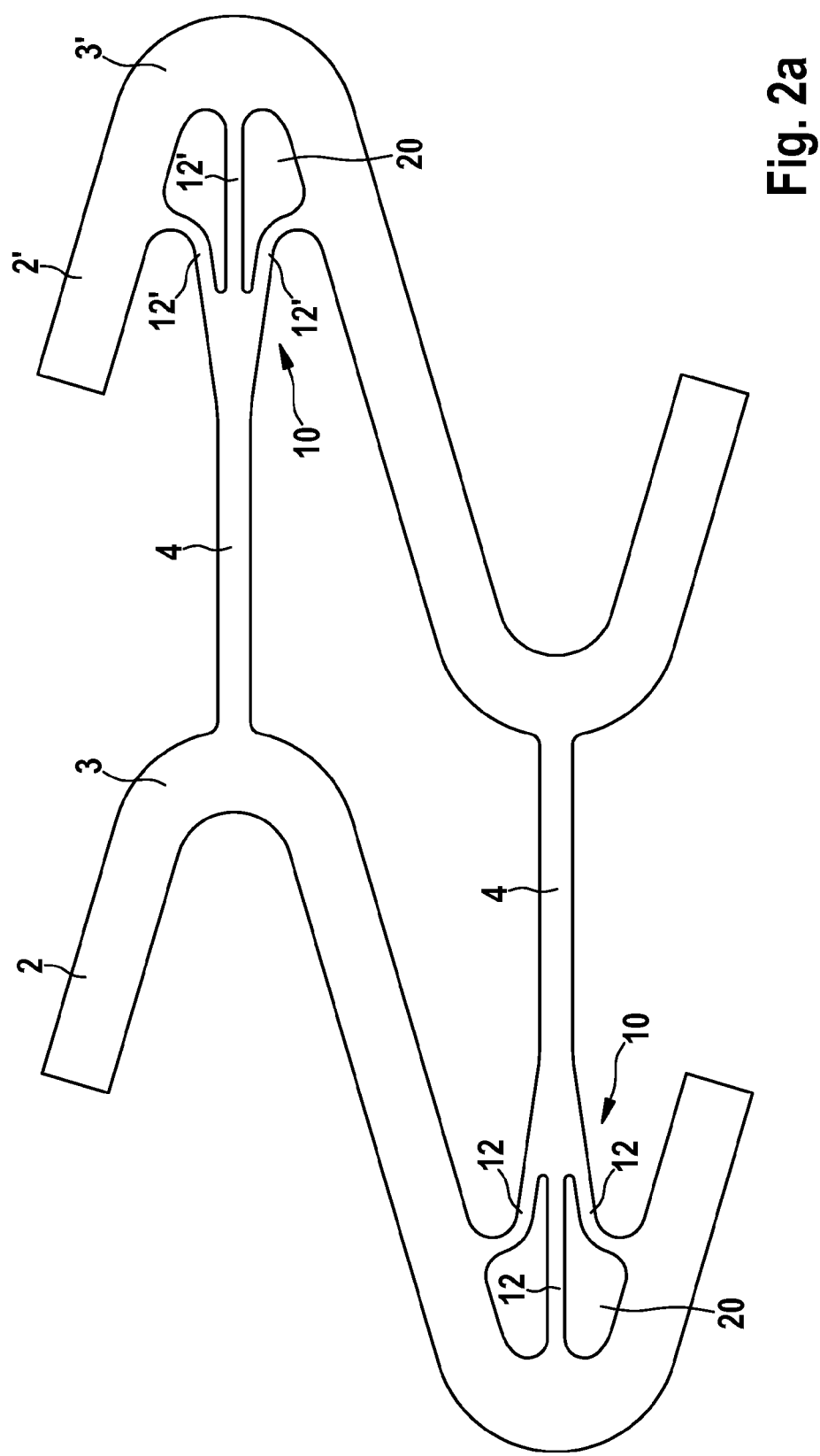
FIGS. 2a and 2b schematically show sections of a base body of a stent according to the invention, wherein the at least double-arm structure consists of exactly three arms.
Figure 2B:
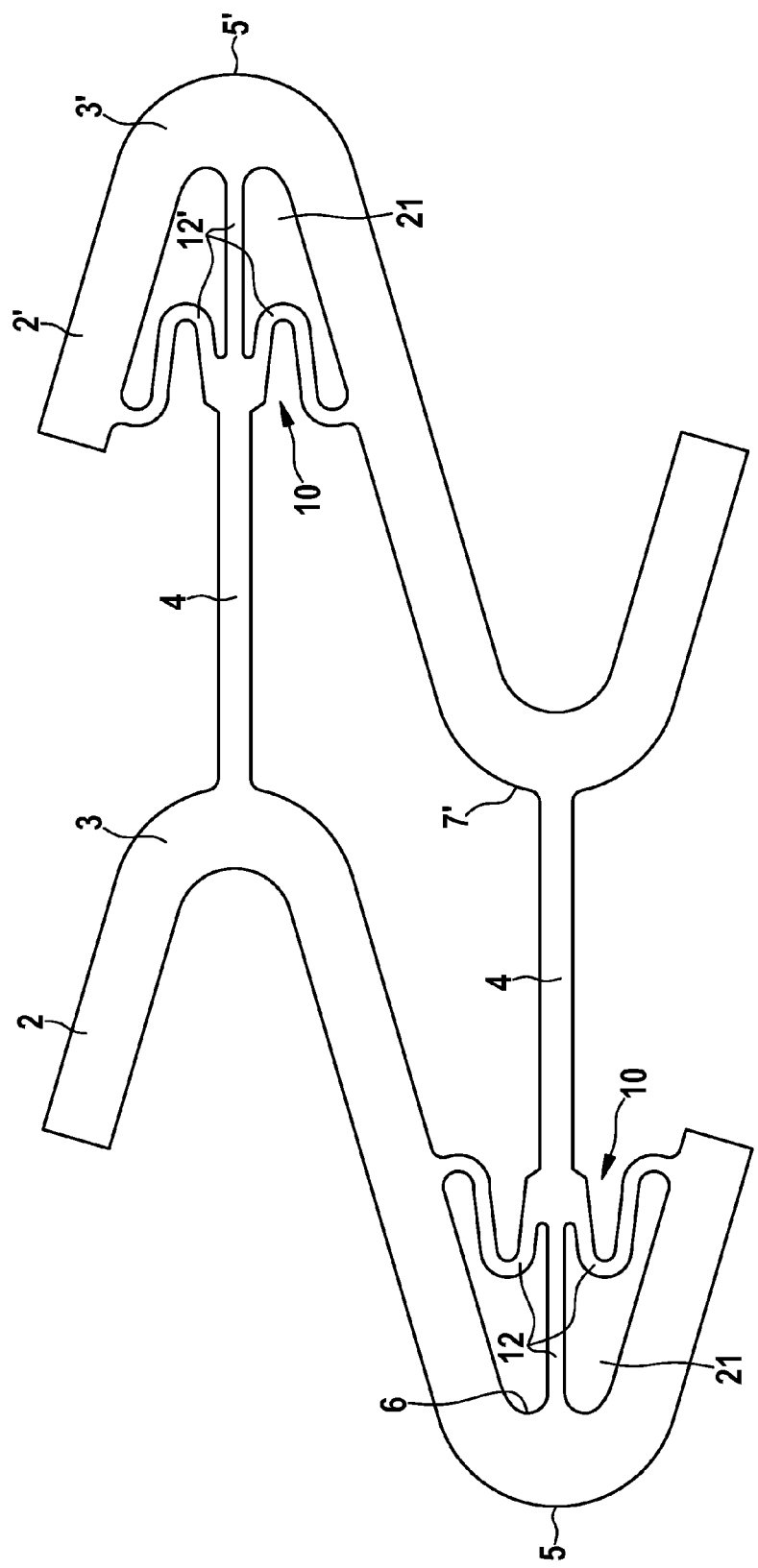

FIGS. 2a and 2b show sections of a base body of a stent according to the invention. What is shown are sections of two meander-shaped struts 2 and 2' disposed in the circumferential direction U and arrayed on one another in the axial direction A, which are connected with each other through axial connectors 4. The meander-shaped struts 2 and 2' have meandering curves 3 and 3'. The meandering curves 3 and 3' show zenith points 5 and 5', having an inside radius 6 and an outside radius 7. The axial connectors 4 connect the inside radius 6 of the zenith point 5 with the outside radius 7 of the zenith point 5' of the meander-shaped strut 2' adjacent in the axial direction A. The at least double-arm structure is accomplished in FIGS. 2a and 2b by means of three arms 12 and 12', respectively, so that a three-armed structure is created. The axial connector 4 is composed of a main stem 8 and the three-armed structure 10. The main stem 8 of the axial connector passes directly and immediately into the three-armed structure 10. This is a joining design having ladle-shaped apertures 20 (FIG. 2a) and a design wherein the apertures enclosed by arms 12 and 12', respectively, together with the meander-shaped struts 2 and 2', respectively, have a chandelier-like shape 21 (FIG. 2b).

Figure 3:
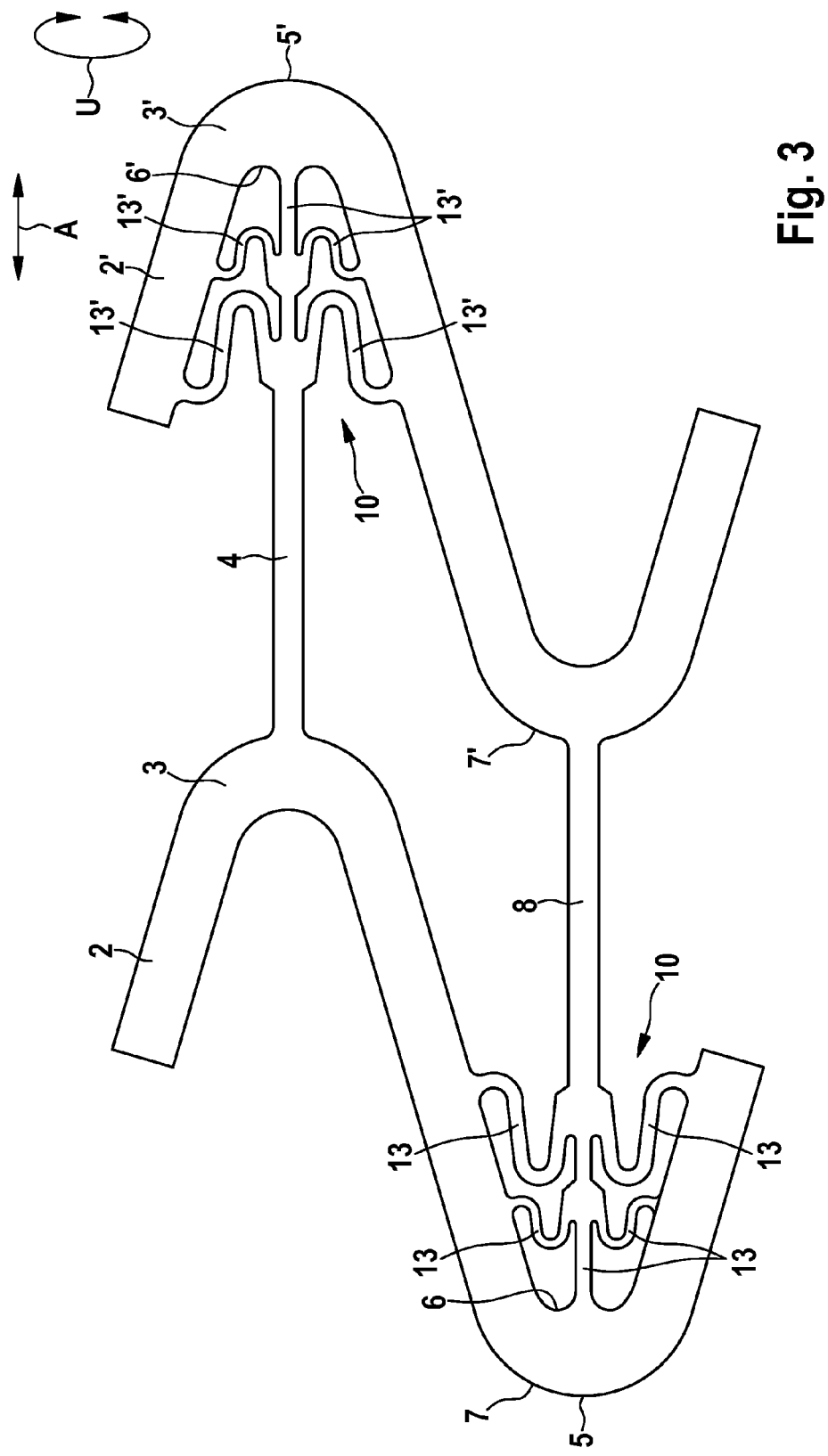
FIG. 3 schematically shows a section of a base body of a stent according to the invention, wherein the at least double-arm structure consists of a ramification of the axial connector having five arms.

FIG. 3 is a section of a base body of a stent according to the invention. What is shown are sections of two meander-shaped struts 2 and 2' disposed in the circumferential direction U and arrayed on one another in the axial direction A, which are connected with each other through axial connectors 4. The meander-shaped struts 2 and 2' have meandering curves 3 and 3'. The meandering curves 3 and 3' show zenith points 5 and 5', having an inside radius 6 and an outside radius 7, 7'. The axial connectors 4 connect the inside radius 6 of the zenith point 5 with the outside radius 7' of the zenith point 5' of the meander-shaped strut 2' adjacent in the axial direction A. The at least double-arm structure in FIG. 3 is accomplished by means of five arms 13 and 13'. The axial connector 4 is composed of a main stem 8 and the ramification of the at least double-arm structure 10. The main stem 8 of the axial connector passes directly and immediately into the five arms 13 and 13', respectively, of the at least double-arm structure 10.

In the embodiment including a five-armed structure, the five arms 13 and 13', respectively, together with the inside radius 6 and 6', respectively, of the zenith point of the meandering curve, define an aperture having a chandelier-like shape.

Besides non-degradable metallic alloys, degradable metals and their alloys may also be used for implementing the invention. The alloys of the elements magnesium, iron, zinc or tungsten are selected such in a composition as to be biodegradable. For the purposes of this invention, "biodegradable" is used to denote such alloys that undergo degradation in a physiological environment, eventually resulting in loss of mechanical integrity of the entire implant or the part of the implant made of said material. For testing the degradation behavior of an alloy in question, artificial plasma is used as a test medium, as prescribed under EN ISO 10993-15:2000 for biodegradation testing (composition NaCl 6.8 g/l, $CaCl_2$ 0.2 g/l, KCl 0.4 g/l, $MgSO_4$ 0.1 g/l, $NaHCO_3$ 2.2 g/l, $Na_2HPO_4$ 0.126 g/l, $NaH_2PO_4$ 0.026 g/l). A sample of the alloy to be tested is stored in a closed test container with a defined amount of test medium at 37° C. At time intervals from between a few hours to several months, adjusted to the degradation behavior to be expected, samples are taken and examined in a known fashion for traces of degradation. The artificial plasma according to EN ISO 10993-15:2000 corresponds to a blood-like medium, and thus provides a chance to reproduceably imitate a physiological environment for the purposes of the invention.

The term "degradation" presently refers to the reaction of a metallic material with its environment, wherein a measurable change of the material is caused, resulting, if the material is used in a component, in an impaired function of the component. A degradation system presently consists of the degrading metallic material as well as a liquid degradation medium, which in its composition imitates the conditions in a physiological environment or is in itself a physiological medium, in particular blood. Factors influencing degradation as far as the material is concerned are, e.g., the composition and pretreatment of the alloy, micro- and submicroscopical inhomogeneities, fringe properties, temperature and stress conditions, and in particular the composition of a surface coating layer. As for the medium, the degradation process is influenced by conductibility, temperature, temperature gradients, acidity, volume-to-surface ratio, differences in concentration, and flow rate.

DE 197 31 021 A1 discloses suitable biodegradable metallic implant materials whose main component is an element from the group of alkali metals, earth alkali metals, iron, zinc, and aluminum. Alloys on the basis of magnesium, iron and zinc are described as being particularly suitable. Secondary components of the alloys may be manganese, cobalt, nickel, chromium, copper, cadmium, lead, tin, thorium, zirconium, silver, gold, palladium, platinum, silicon, calcium, lithium, aluminum, zinc, and iron. From DE 102 53 634 A1 it is further known to use a biodegradable magnesium alloy with a content of magnesium >90%, yttrium 3.7-5.5%, rare earth metals 1.5-4.4%, and the rest <1%, which is particularly suited for the production of an endoprosthesis, e.g. in the form of a self-expanding or balloon-expandable stent.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE NUMBERS

A axial direction
U circumferential direction
2 meander-shaped strut
3, 3' meandering curves
4 axial connector
5, 5' zenith point
6, 6' inside radius of the zenith point
7, 7' outside radius of the zenith point
8 main stem of the axial connector 4
10 at least double-arm structure
11, 11' arms of the at least double-arm structure 10
12, 12' arms of the at least double-arm structure 10 in the case of three arms
13 arms of the at least double-arm structure 10 in the case of five arms
20 ladle-shaped aperture
21 chandelier-shaped aperture

What is claimed is:

1. A stent having a base body circumscribing a cylindrical shape and radially expandable from a contracted starting position into a dilated support position, comprising:
   a) a plurality of struts, each strut comprising alternating curves separated by a straight segment, the struts being disposed in the circumferential direction and arrayed such that an inside zenith point of a first curve is aligned in the axial direction of the stent with an inside zenith point of a second curve on an adjacent strut, each strut being made of a flexible material; and
   b) at least one axial connector in the axial direction, connecting the struts of the two axially adjacent curves;
   wherein the at least one axial connector connects the inside radius of the zenith point of the first curve directly to the inside radius of the zenith point of the second curve;

wherein the at least one axial connector at the inside radius of the zenith point of the first curve has at least two arms forming an at least double-arm structure.

2. The stent according to claim 1, wherein the at least double-arm structure has two arms enclosing in the dilated support position an angle in the range of 30° to 180° between the two arms.

3. The stent according to claim 2, wherein the angle is in the range of 60° to 180° between the two arms.

4. The stent according to claim 3, wherein the angle is in the range of 90° to 180° between the two arms.

5. The stent according to claim 1, wherein the at least double-arm structure has three arms, wherein one arm, optionally the middle one, runs parallel to the axial direction.

6. The stent according to claim 1, wherein the flexible material is a material selected from the group consisting of metals, metal alloys and polymers.

7. The stent according to claim 1, wherein the flexible material is a biodegradable material.

8. The stent according to claim 7, wherein the biodegradable material is a material selected from the group consisting of magnesium, iron, zinc, tungsten and a metal alloy of any combination thereof.

9. The stent according to claim 1, wherein the at least one axial connector comprises a linear segment parallel to the axial direction of the stent.

10. The stent according to claim 9, wherein the linear segment comprises a double armed structure at each opposing end.

\* \* \* \* \*